(12) United States Patent
Sias et al.

(10) Patent No.: US 7,008,592 B2
(45) Date of Patent: *Mar. 7, 2006

(54) DECONTAMINATION APPARATUS AND METHOD USING AN ACTIVATED CLEANING FLUID MIST

(75) Inventors: Ralph M. Sias, Oceanside, CA (US); Heath E. Sias, Oceanside, CA (US); Stanley J. Diniz, Vista, CA (US); Fernando Guerrero, Vista, CA (US); J. Michael Pierce, Oro Valley, AZ (US); Louis Montulli, Vista, CA (US)

(73) Assignee: Intecon Systems, Inc., Carlsbad, CA (US)

( * ) Notice: Subject to any disclaimer, the term of this patent is extended or adjusted under 35 U.S.C. 154(b) by 577 days.

This patent is subject to a terminal disclaimer.

(21) Appl. No.: 10/003,592

(22) Filed: Nov. 1, 2001

(65) Prior Publication Data

US 2003/0035754 A1 Feb. 20, 2003

Related U.S. Application Data

(63) Continuation-in-part of application No. 09/564,290, filed on May 3, 2000, now Pat. No. 6,706,243, which is a continuation-in-part of application No. 09/306,519, filed on May 6, 1999, now Pat. No. 6,343,425.

(51) Int. Cl.
*A61L 2/00* (2006.01)

(52) U.S. Cl. .............. 422/28; 422/1; 422/2; 422/4; 422/40; 422/186; 422/186.04

(58) Field of Classification Search ............ 134/200, 134/201; 422/121, 186.04, 186, 292, 29, 422/28, 22

See application file for complete search history.

(56) References Cited

U.S. PATENT DOCUMENTS

| | | | |
|---|---|---|---|
| 3,992,221 A | 11/1976 | Homsy et al. | |
| 4,366,125 A | 12/1982 | Kodera et al. | |
| 4,643,876 A | 2/1987 | Jacobs et al. | |
| 4,670,010 A | 6/1987 | Dragone | |
| 4,704,942 A * | 11/1987 | Barditch | 89/1.11 |
| 4,817,800 A | 4/1989 | Williams et al. | |
| 4,818,488 A | 4/1989 | Jacob | |
| 5,058,785 A | 10/1991 | Rich et al. | |
| 5,074,322 A | 12/1991 | Jaw | |
| 5,084,239 A | 1/1992 | Moulton et al. | |
| 5,095,925 A | 3/1992 | Elledge et al. | |
| 5,115,166 A | 5/1992 | Campbell et al. | |
| 5,178,829 A | 1/1993 | Moulton et al. | |
| 5,184,046 A | 2/1993 | Campbell | |

(Continued)

OTHER PUBLICATIONS

Giles Dillingham et al., "Plasma Processing", *PC*, Dec. 1998, pp. 10-15.

(Continued)

*Primary Examiner*—Krisanne Jastrzab
(74) *Attorney, Agent, or Firm*—Jones, Tullar&Cooper, P.C.

(57) ABSTRACT

Decontamination is achieved by producing an activated cleaning fluid mist using a decontamination apparatus having a source of a cleaning fluid, a mist generator having an input flow of the cleaning fluid and an output flow of a mist of the cleaning fluid at substantially one atmosphere ambient pressure, and an activator positioned to activate the mist of the cleaning fluid to produce the activated cleaning fluid mist wherein atoms of the cleaning fluid are activated. The activated cleaning fluid mist is contacted to a location to be decontaminated.

18 Claims, 5 Drawing Sheets

U.S. PATENT DOCUMENTS

| | | | |
|---|---|---|---|
| 5,288,460 A | 2/1994 | Caputo et al. | |
| 5,382,410 A | * 1/1995 | Peltier | 422/121 |
| 5,393,490 A | 2/1995 | Jacob | |
| 5,516,369 A | 5/1996 | Lur et al. | |
| 5,604,993 A | 2/1997 | Auckerman | |
| 5,622,595 A | 4/1997 | Gupta et al. | |
| 5,648,046 A | * 7/1997 | Weibel | 422/4 |
| 5,667,753 A | 9/1997 | Jacobs et al. | |
| 5,700,327 A | 12/1997 | Babacz et al. | |
| 5,750,072 A | 5/1998 | Sangster | |
| 5,770,000 A | 6/1998 | Zinman et al. | |
| 5,858,108 A | 1/1999 | Hwang | |
| 5,876,666 A | 3/1999 | Lin et al. | |
| 5,882,611 A | 3/1999 | Williams et al. | |
| 5,935,339 A | 8/1999 | Henderson et al. | |
| 5,942,438 A | 8/1999 | Antonoplos et al. | |
| 5,975,094 A | 11/1999 | Shurtliff | |
| 5,983,704 A | 11/1999 | Park et al. | |
| 6,017,414 A | 1/2000 | Koemtzopoulos et al. | |
| 6,062,976 A | 5/2000 | DeGuzman | |
| 6,706,243 B1 | * 3/2004 | Sias et al. | 422/28 |

OTHER PUBLICATIONS

"University-backed project shoots for 'green' cleaning breakthrough", *Micro*, Apr. 1999, pp. 12-17.

Lynn Kuntz, "Ingredients to Raise the Microbial Bar", Food Product, Apr. 1999, Internet publication at http://www.foodproductdesign.com/current/0499ap.html, pp. 1-8.

* cited by examiner

DECONTAMINATION APPARATUS AND METHOD USING AN ACTIVATED CLEANING FLUID MIST

This application is a continuation in part of allowed application Ser. No. 09/564,290, filed May 3, 2000, now U.S. Pat. No. 6,706,243, for which priority is claimed and whose disclosure is incorporated by reference, which in turn is a continuation in part of allowed application Ser. No. 09/306,519, filed May 6, 1999, now U.S. Pat. No. 6,343,425, for which priority is claimed and whose disclosure is incorporated by reference.

This invention relates to an approach for decontaminating articles, enclosed spaces, and unenclosed spaces and, more particularly, to microbiological decontamination of such locations.

BACKGROUND OF THE INVENTION

Microbiological species are widely distributed in our environment. Most microbiological species are of little concern, because they do not damage other living organisms. However, other microbiological species may infect man or animals and cause them harm.

The removing or rendering ineffective of injurious microbiological organisms has long been of interest. Drugs and medical devices are sterilized and packaged in sterile containers. Medical environments such as operating rooms, wards, and examination rooms are decontaminated by various cleaning procedures so that injurious microbiological organisms cannot spread from one patient to another. Wounds are sterilized to prevent infection.

Most prior situations requiring decontamination of injurious microbiological organisms have been relatively well controlled, where all parties wished to achieve the decontamination and cooperated in the decontamination effort. More recently, biological warfare and bioterrorism have become of increasing concern. In these circumstances, injurious microbiological organisms may be intentionally released into a population, with the intent to disseminate the microbiological organisms as widely as possible and to cause as much harm as possible in the population. The microbiological organisms are typically selected so that tiny amounts of the microbiological organisms achieve the maximum contamination, the microbiological organisms may be disseminated widely, the microbiological organisms can exist for extended periods of time in a dormant state before becoming active to cause injury, and the microbiological organisms are difficult to control and eradicate.

The available technologies for controlling microbiological organisms, developed for relatively small-scale use in well-controlled environments and where there is not an overt attempt to spread the microbiological organisms, are of limited value in these public health circumstances of biological warfare and bioterrorism. A new approach is needed that is more readily usable in a variety of less-well-controlled environments. The present invention fulfills this need, and further provides related advantages.

SUMMARY OF THE INVENTION

The present invention provides an apparatus and method for achieving decontamination of environments and articles from microbiological organisms. The approach achieves the decontamination rapidly, and typically on contact. The decontaminant is distributed on an air-borne mechanism, so that it reaches the same locations as air-borne microbiological organisms. It does not require a line of sight to the contaminated region, so that the microbiological organisms cannot escape destruction in hidden locations. The present approach may be readily scaled from small to large sizes of apparatus and decontaminated regions, and it may be used for both civilian and military applications. It may be used within enclosures to decontaminate articles or flows of gases. It may be used to decontaminate enclosed spaces, such as interiors of rooms and ventilating systems. It may be used in open spaces to decontaminate entire areas. The decontamination is achieved without using persistent chemicals that themselves may be toxic and cause harm, or leave residues. The decontamination operates by a mechanism that does not cause mutation of the biological microorganism toward a decontamination-resistant strain. The present approach, while directed primarily toward biological microorganisms, also removes particulate matter, which may serve as the delivery system for the biological microorganisms, from surfaces.

In accordance with the invention, a decontamination apparatus comprises a source of a cleaning fluid (preferably a liquid), a mist generator having an input flow of the cleaning fluid and an output flow of a mist of the cleaning fluid at substantially one atmosphere ambient pressure, and an activator positioned to activate the mist of the cleaning fluid to produce an activated cleaning fluid mist.

The cleaning fluid preferably comprises a source of an active species. The preferred active species is hydroxyl ions, and the preferred source is hydrogen peroxide. The source may instead be a more-complex species that produces hydroxyl ions upon reaction or decomposition. Examples of such more-complex species include peracetic acid ($CH_2COO-OH+H_2O$), sodium percarbonate ($2Na_2CO_3+3H_2O_2$), and gluteraldehyde ($C_5H_8O_2$). The cleaning fluid may further include promoting species that aid the active species in accomplishing its attack upon the biological microorganisms. Examples of such promoting species include ethylenediaminetetraacetate, isopropyl alcohol, enzymes, fatty acids, and acids.

The mist generator may be any device that generates a mist of the cleaning fluid, such as a nebulizer or a spray nozzle. The mist generator may produce an overpressure of the cleaning mist, so that it is above one atmosphere as it emerges from the mist generator. The overpressure aids in distributing the cleaning mist into the atmospheric environment. This initial overpressure prior to distribution of the cleaning mist into the atmosphere at one atmosphere pressure is within the scope of "substantially one atmosphere ambient pressure".

The activator activates the cleaning fluid to an activated condition such as the ionized, plasma, or free radical states which, with the passage of time, returns to the non-activated state (a process termed "recombination"). To accomplish the activation, the activator produces activating energy such as electric energy or photonic energy. The photonic energy may be produced by a laser. Examples of activators include an AC electric field, an AC arc, a DC electric field, a pulsed DC electric field, a DC arc, an electron beam, an ion beam, a microwave beam, a radio frequency beam, and an ultraviolet light beam. The activator may include a tuner that tunes the amplitude, frequency, wave form, or other characteristic of the activating energy to achieve a desired, usually a maximum, re-combination time of the activated cleaning fluid mist.

The mist generator and the activator may be disposed proximally, so that the activator activates the mist of the cleaning fluid as it leaves the mist generator. That is, the activator may activate the mist as it flows from the mist generator. The activator may instead or additionally be located remotely from the mist generator, so that the mist is generated to fill a space and is then activated. The remote activator may be used to maintain the mist in the activated state for extended periods of time for a heightened effect.

The apparatus may include an enclosure into which the mist of the cleaning fluid is directed by the mist generator. The enclosure may receive articles to be decontaminated, or it may receive a flow of a gas such as air to be decontaminated. The enclosure may instead define an enclosed space, such as room or an interior of a vehicle, which is to be decontaminated. There may instead be no enclosure, so that the activated cleaning fluid mist is directed into free space to decontaminate an unenclosed, open space. The decontamination approach is equally effective in all of these conditions to destroy biological microorganisms, although it is most efficient in terms of the utilization of the cleaning fluid in enclosures and enclosed spaces.

A method for performing decontamination comprises the steps of producing an activated cleaning fluid mist wherein at least a portion of the cleaning fluid mist is in an activated state, and contacting the activated cleaning fluid mist to a location to be decontaminated. The step of producing is preferably performed using the apparatus described previously.

An important feature of the present approach is that the apparatus and method operate at substantially one atmosphere pressure in the ambient environment. Some earlier decontamination systems operated in a vacuum, which is useful for decontaminating objects that may be placed into a vacuum chamber but is impractical for decontaminating objects and areas that cannot be evacuated. "Ambient pressure" means the pressure in the environment surrounding the apparatus. In most embodiments, the apparatus itself generates a relatively small positive pressure to propel the activated cleaning fluid mist from the apparatus, but that does not change the fact that the environment in which the apparatus operates is at substantially one atmosphere pressure.

The present approach provides a highly effective technology for achieving decontamination of microbiological organisms. It is effective in both enclosed volumes and spaces, and open spaces. It is therefore effective in many situations where the biological microorganisms have been intentionally spread over wide areas or is intentionally being disseminated. Other features and advantages of the present invention will be apparent from the following more detailed description of the preferred embodiment, taken in conjunction with the accompanying drawings, which illustrate, by way of example, the principles of the invention. The scope of the invention is not, however, limited to this preferred embodiment.

DETAILED DESCRIPTION OF THE INVENTION

Figure 1:
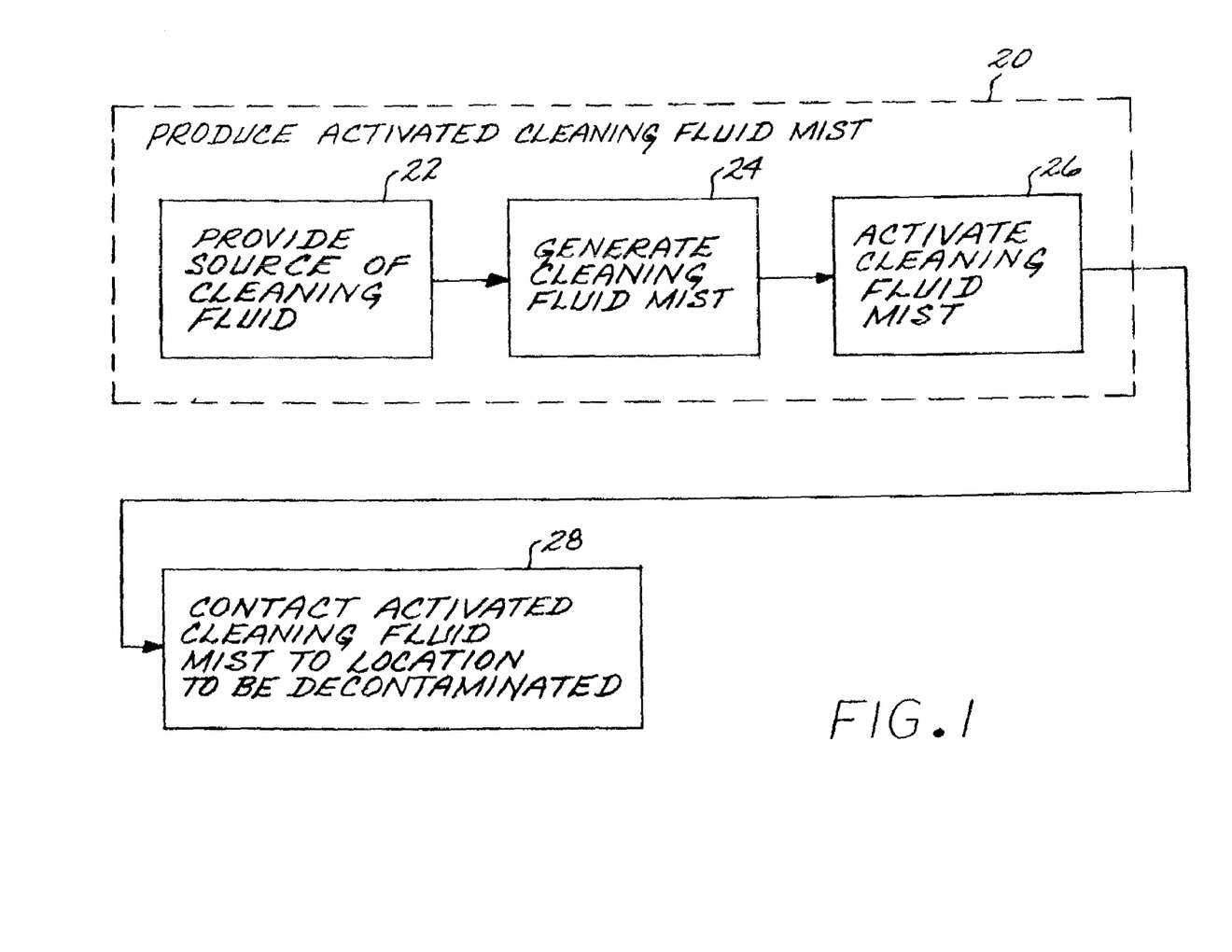
FIG. 1 is a block flow diagram of a preferred approach for practicing the invention.

FIG. 1 depicts a preferred method for performing decontamination. An activated cleaning fluid mist is produced, numeral 20. Any operable approach may be used, and a preferred approach is illustrated within step 20 of FIG. 1. A source of a cleaning fluid is provided, numeral 22. The cleaning fluid is preferably a liquid that may be vaporized in ambient-pressure air to form a mist. The liquid cleaning fluid may be stored at one atmosphere or slightly greater pressure, while a cleaning fluid in a gaseous state usually requires pressurized storage. The source of the cleaning fluid may also be a precursor of the cleaning fluid, such as a solid, liquid, or gas that reacts, decomposes, or otherwise produces the cleaning fluid.

The cleaning fluid is of any operable type. The cleaning fluid must contain an activatable species. A preferred cleaning fluid comprises a source of hydroxyl ions ($OH^-$) for subsequent activation. Such a source may be hydrogen peroxide ($H_2O_2$) or a precursor species that produces hydroxyl ions. Hydrogen peroxide that is preferably used in the present approach to produce hydroxyl ions is effective in rapidly destroying many types of biological microorganisms, is an aqueous solution, decomposes ultimately to oxygen and water, leaves no chemical residue after decomposition, is nontoxic and harmless to man and animals in both its original and decomposed states, and is inexpensive and readily available.

Other sources of hydroxyl ions may be used as appropriate. Examples of other operable sources of hydroxyl ions include peracetic acid ($CH_2COO$—$OH+H_2O$), sodium percarbonate ($2Na_2CO_3+3H_2O_2$), and gluteraldehyde ($C_5H_8O_2$).

Other activatable species and sources of such other activatable species may also be used.

The activated species such as the activated hydroxyl species desirably attack the cell wall of the microbiological organism (microbe) by a redox reaction. This approach to preventing the microbes from multiplying and killing the microbes does not function through an attack on DNA, so that there is no resulting mutation of the DNA. Consequently, the microbes are not expected to become resistant to the attack due to mutations over time.

The cleaning fluid may also contain promoting species that are not themselves sources of activatable species such as hydroxyl ions, but instead modify the decontamination reactions in some beneficial fashion. Examples include ethylenediaminetetraacetate (EDTA), which binds metal ions and allows the activated species to destroy the cell walls more readily; an alcohol such as isopropyl alcohol, which improves wetting of the mist to the cells; enzymes, which speed up or intensity the redox reaction in which the activated species attacks the cell walls; fatty acids, which act as an ancillary anti-microbial and may combine with free radicals to create residual anti-microbial activity; and acids such as citric acid, lactic acid, or oxalic acid, which speed up or intensity the redox reaction and may act as ancillary anti-microbial species to pH-sensitive organisms. Mixtures of the various activatable species and the various promoting species may be used as well. The cleaning fluids are preferably aqueous solutions, but may be solutions in organics such as alcohol. The cleaning fluid source may be a source of the cleaning fluid itself, or a source of a cleaning fluid precursor that chemically reacts or decomposes to produce the cleaning fluid.

A cleaning fluid mist, containing the activatable species and the promoting species, if any, is generated, numeral 24. The mist generator to generate the cleaning fluid mist may be of any operable type. In the preferred case, the cleaning mist or vapor is fine droplets of the vaporized cleaning fluid. The droplets are preferably roughly uniformly sized, on the order of from about 1 to about 20 micrometers in diameter. Various types of mist generators have been used in prototype studies. One type is a nebulizer, such as a low-pressure ultrasonic nebulizer. An example is the commercially available Model SCA2000X made by Stultz. The nebulizer achieves mist formation by subjecting a flow of the cleaning fluid to ultrasonic energy. The ultrasonic energy introduced by this type of nebulizer also aids in dissociation of the molecules of the vaporized activatable species, and lowers the electromagnetic energy required to achieve activation of the molecules. A nonultrasonic nebulizer may be used. The mist generator may instead be a spray head such as a high-pressure spray head that establishes ultrasonic waves in the vaporized cleaning material, leading to a higher dissociation and subsequent ionic activity. The mist generator may instead be a spray system such as the IVEK Digispense 800 System.

In those cases where two or more cleaning fluids or components of the cleaning fluid are used, the cleaning fluids may be mixed together and vaporized in a single mist generator. However, in other cases the components of the cleaning fluid are not compatibly vaporized, and a separate mist generator is provided for each cleaning fluid. A commercial mist generator is typically tuned for the specific fluid to be vaporized into a mist, so that optimal vapor production occurs only for that specific fluid or closely similar fluids. If multiple cleaning fluids or components of cleaning fluids are used with substantially different fluid and vaporization properties, it is usually necessary to provide a separate mist generator for each of the flows of cleaning fluid. The discussion of mist generator in relation to the subsequently discussed embodiments includes both single and multiple mist generators used together.

The cleaning fluid mist is activated to produce an activated cleaning fluid mist, numeral 26. The activation produces activated species of the cleaning fluid material in the mist, such as the cleaning fluid material in the ionized, plasma, or free radical states. At least a portion of the activatable species is activated, and in some cases some of the promoting species, if any, is activated. A high yield of activated species is desired to improve the efficiency of the decontamination process, but it is not necessary that all or even a majority of the activatable species achieve the activated state. Any operable activator may be used. The activator field or beam may be electrical or photonic. Examples include an AC electric field, an AC arc, a DC electric field, a pulsed DC electric field, a DC arc, an electron beam, an ion beam, a microwave beam, a radio frequency beam, and an ultraviolet light beam produced by a laser or other source. The activator causes at least some of the activatable species of the cleaning fluid in the cleaning fluid mist to be excited to the ion, plasma, or free radical state, thereby achieving "activation". These activated species enter redox reactions with the cell walls of the microbiological organisms, thereby destroying the cells or at least preventing their multiplication and growth. In the case of the preferred hydrogen peroxide, at least some of the $H_2O_2$ molecules dissociate to produce hydroxyl ($OH^-$) and monatomic oxygen ($O^-$) ionic activated species. These activated species remain dissociated for a period of time, typically several seconds or longer, during which they attack and destroy the biological microorganisms. The activator is preferably tunable as to the frequency, waveform, amplitude, or other properties of the activation field or beam, so that it may be optimized for achieving a maximum recombination time for action against the biological microorganisms. In the case of hydrogen peroxide, the dissociated activated species recombine to form diatomic oxygen and water, harmless molecules.

Figure 2:
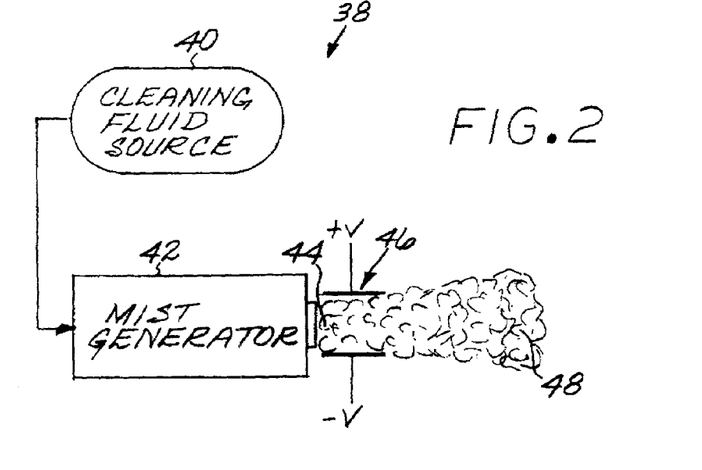
FIG. 2 is a schematic view of a first embodiment of apparatus for practicing the invention, with the activator proximally located to the mist generator.
Figure 3:
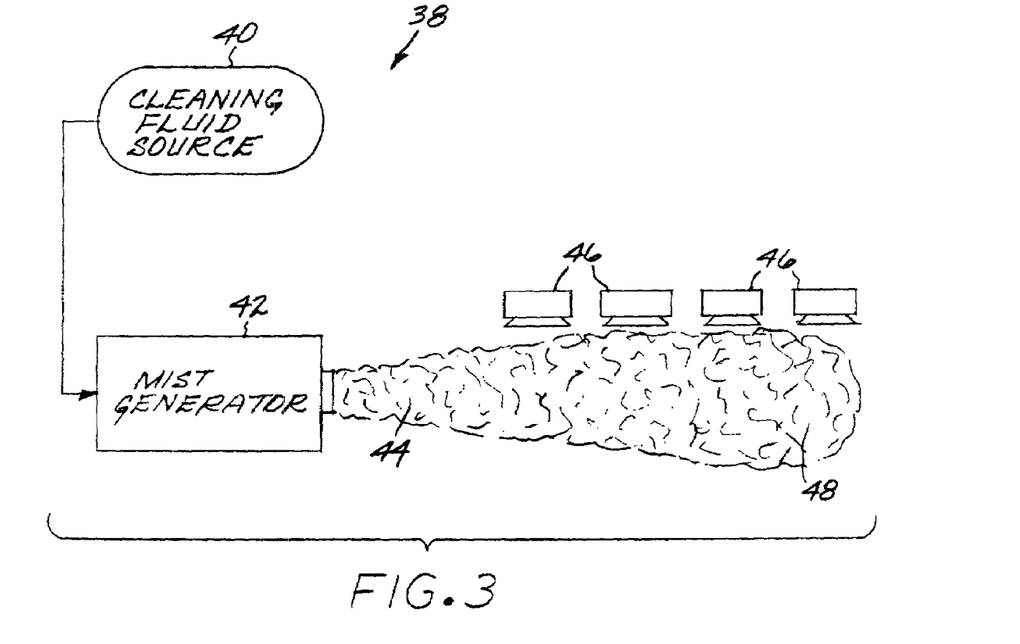
FIG. 3 is a schematic view of a second embodiment of apparatus for practicing the invention, with the activator located remotely from the mist generator.
Figure 4:
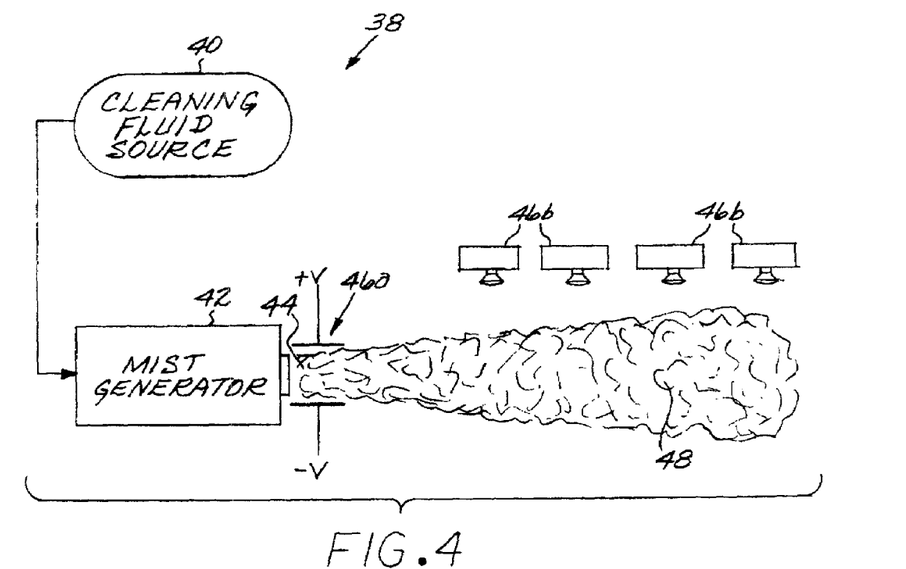
FIG. 4 is a schematic view of a third embodiment of apparatus for practicing the invention, with both proximate and remote activators.

The physical relationship of the mist generator and the activator may be of several types, illustrated schematically for three types of decontamination apparatus 38 in FIGS. 2–4. A source of the cleaning fluid 40 provides a flow of the cleaning fluid to a mist generator 42 in each case. The mist generator forms a cleaning fluid mist 44 of the cleaning fluid. The cleaning fluid mist 44 includes the activatable species and the promoting species, if any. In the embodiment of FIG. 2, an activator 46, schematically illustrated as a pair of electrical discharge plates between which the cleaning fluid mist 44 passes, is located proximate to, and preferably immediately adjacent to, the mist generator 42. The mist generator 42 and the activator 46 are typically packaged together for convenience in a single housing in this case. The cleaning fluid mist 44 leaving the mist generator 42 is immediately activated by the activator 46 to produce an activated cleaning fluid mist 48. In the embodiment of FIG. 3, the activator 46, here schematically illustrated as a set of microwave sources, is located remotely from the mist generator 42. The cleaning fluid mist 44 flows from mist generator 42 and remains as a non-activated cleaning fluid mist for a period of time, prior to passing into a region where it is in the influence of and activated by the activator 46. These two embodiments may be combined as shown in FIG. 4, where the cleaning fluid mist 44 is initially activated to form the activated cleaning fluid mist 48 by an activator 46a that is proximate to the mist generator 42, and then kept in the activated state or re-activated as necessary by an activator 46b that is remote from the mist generator 42. In this case, the activator 46b is illustrated to be an ultraviolet light source. The apparatus of FIG. 4 has the advantage that the cleaning fluid is initially activated and then maintained in an activated state for an extended period of time to achieve a prolonged effective state. These various types of apparatus 38 are used in differing situations according to the physical constraints of each situation, and some illustrative situations are discussed subsequently. Particle and/or gas filters may be provided where appropriate to remove particulate matter that is the carrier for microbiological organisms, and also to remove the residual cleaning mist and its reaction products.

The activated cleaning fluid mist 48 is contacted to locations that are to be decontaminated, numeral 28. The types of locations and the manner of contacting lead to a number of specific embodiments of the previously described general approaches, as described next.

Figure 5:
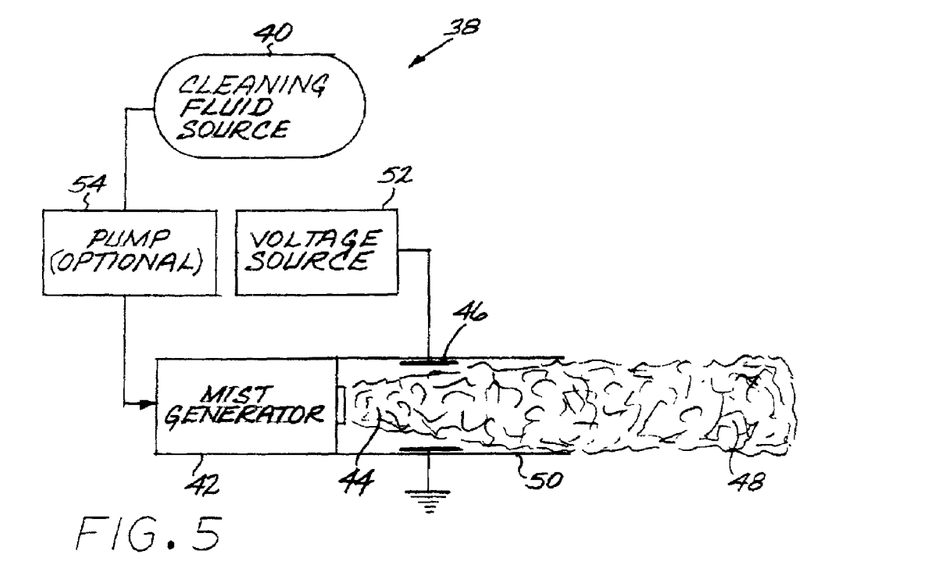
FIG. 5 illustrates a streaming decontamination apparatus.
Figure 6:
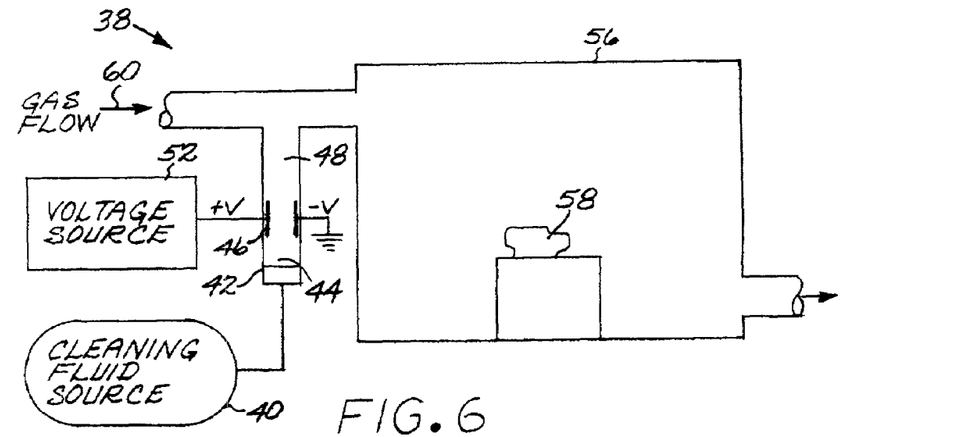
FIG. 6 illustrates a chamber-based decontamination apparatus.
Figure 7:
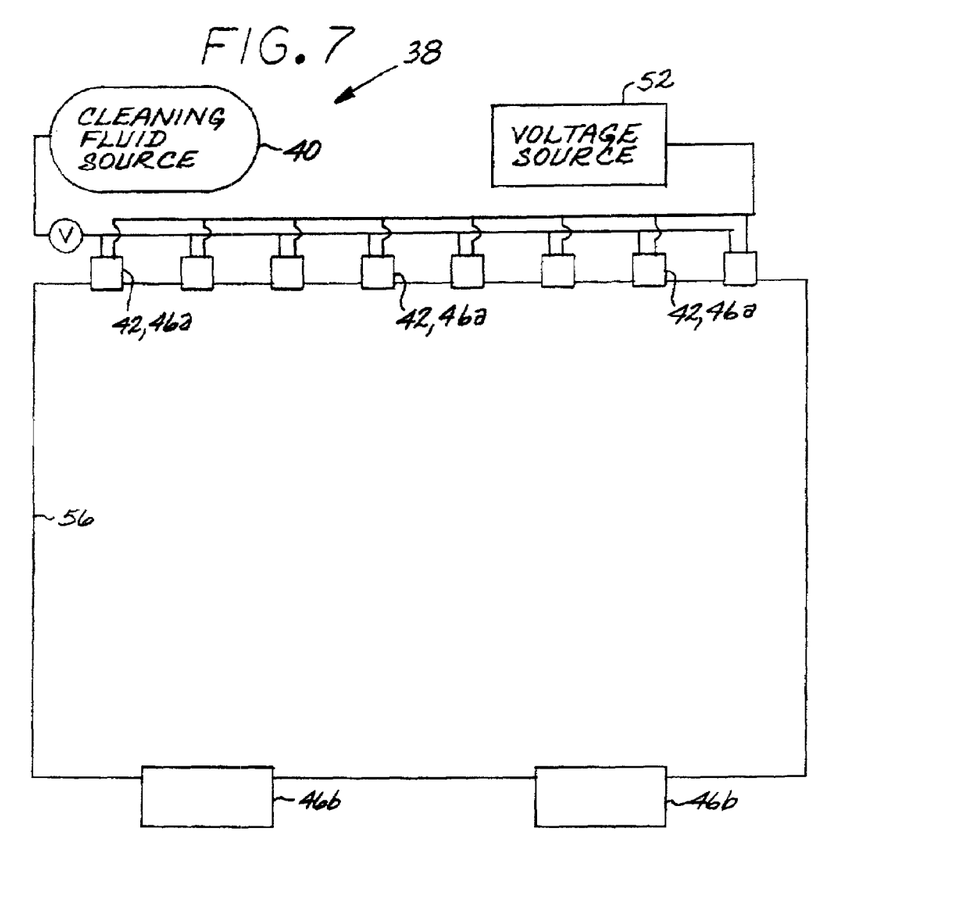
FIG. 7 illustrates a decontamination apparatus for decontaminating a room.
Figure 8:
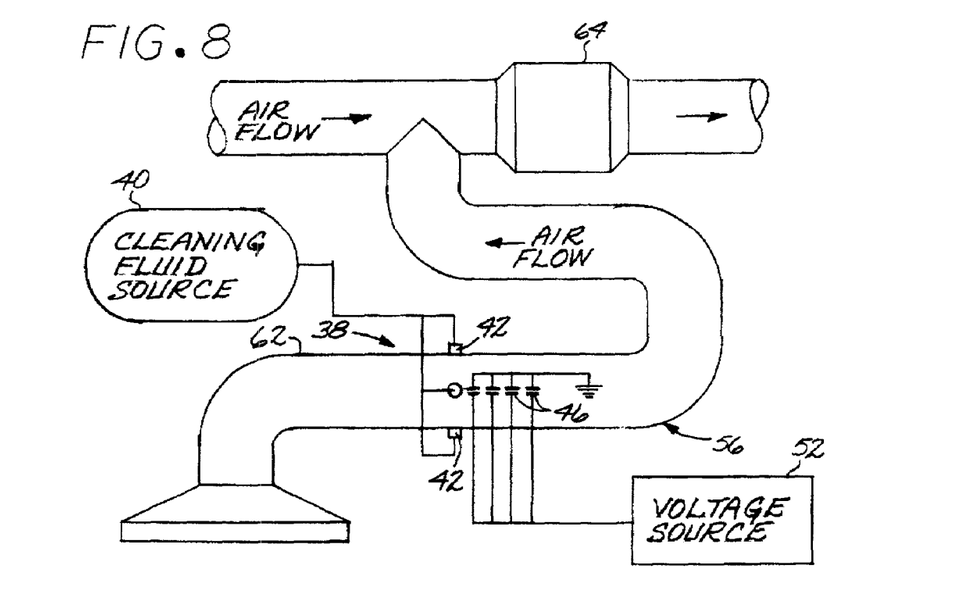
FIG. 8 illustrates a decontamination apparatus for a heating, ventilating, and air conditioning duct system.
Figure 9:
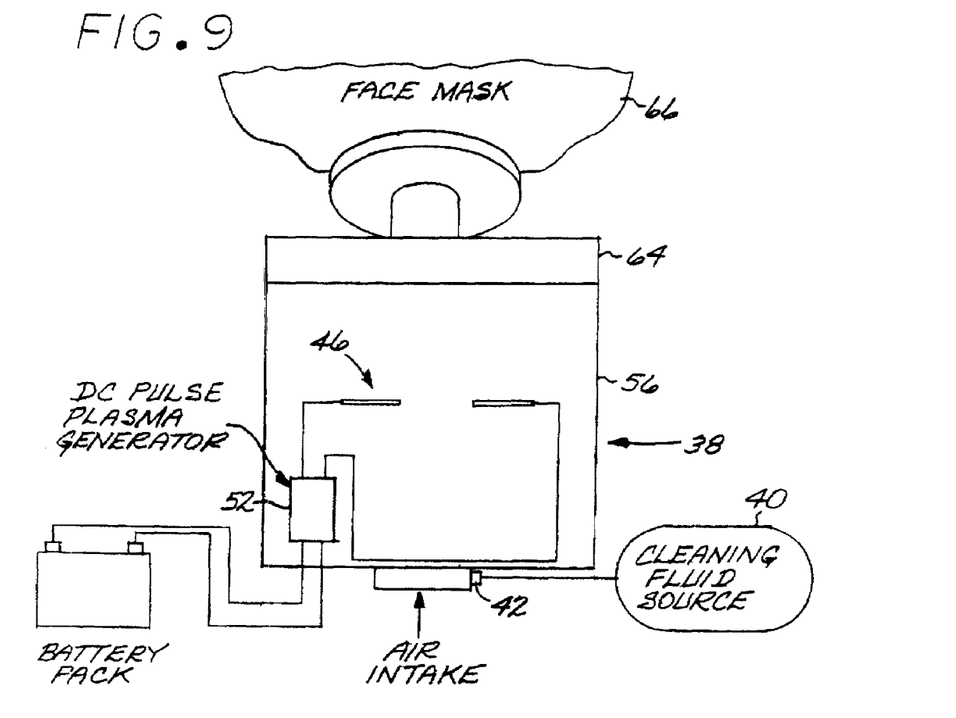
FIG. 9 illustrates a decontamination apparatus for air breathed by a person.

FIG. 5 illustrates a streaming form of decontamination apparatus 38. This type of apparatus normally uses the general configuration shown in FIG. 2, where the activator 46 is located proximally to the mist generator 42. It does not require an enclosure, although it may be used within an enclosure. In FIG. 5 and other figures illustrating specific embodiments of the apparatus, the common elements of structure will be given the same reference numerals as used elsewhere, and the other description is incorporated into the description of each embodiment. Cleaning fluid from the cleaning fluid source 40 is supplied to the mist generator 42, and the cleaning fluid mist 44 flows from the mist generator 42. The cleaning fluid mist 44 flows through an interior of a tube 50 that channels and directs the flow of the cleaning fluid mist 44. The activator 46 powered by a voltage source 52 activates the cleaning fluid mist 44 as it flows through the interior of the tube 50, so that the activated cleaning fluid mist 48 flows from the tube 50 as a stream. The stream is directed into a volume or against an object that is to be decontaminated.

This basic configuration of FIG. 5 may be scaled over a wide range of sizes. In one example, the cleaning fluid source 40 is a hand-held pressure can of the type commonly used to dispense fluids or gases. The voltage source 52 is a battery and a circuit to supply a high voltage to the activation source 46 for a sufficient period to activate the amount of cleaning fluid that is stored within the pressure can. The tube 50 is the nozzle of the pressure can. In another example, the tube 50 is a hand-held wand operating from a larger-volume cleaning fluid source 40 and with a plug-in or battery electrical voltage source 52. The cleaning fluid source 40 may be pressurized to drive the flow of the cleaning fluid through the tube 50, or there may be provided an optional pump 54 that forces the cleaning fluid through the mist generator 42 and out of the tube 50 with great force. This embodiment may be used to decontaminate objects, wounds, the hands, and the like. The greater the pressure of the cleaning fluid as it passes down the tube 50, the further the distance of projection of the activated cleaning fluid mist 48 before recombination of the activated species occurs. As noted earlier, even where there is such a pressurization, the approach is within the scope of "substantially one atmosphere ambient pressure". In another embodiment, in the form of a man-portable unit, the cleaning fluid source 40 is a tank of cleaning fluid carried on the back of a person in backpack fashion. The backpack also includes the battery-powered voltage source 52 and pump 54, if any, and the tube 50 is in the form of a barrel that may be aimed by the operator. This embodiment may be used as a "man pack" by a mobile decontamination worker in moving from place to place. In yet another embodiment, the entire apparatus 38 is carried on a vehicle. A relatively high pressure pump 54 is typically used (but still "substantially at one atmosphere pressure"), to eject the activated cleaning fluid mist 48 from the tube 50 over a relatively large area in the manner of a water cannon. Because the mist is fine droplets, it does not travel as far as the stream of a water cannon and does not transmit the same high force as does the stream of a water cannon. This vehicle mounted unit is effective in large outdoors areas, for example in driving through a city street and decontaminating the street, the faces of the buildings, and persons in the street.

Other forms of the apparatus 38 are primarily used in conjunction with an enclosure, either to enclose the decontamination processing or an object or flow, or to achieve decontamination of the interior of the enclosure. FIG. 6 illustrates the apparatus 38 including an enclosure 56 that serves as a chamber in which an object 58 is decontaminated. The object 58 may be stationary, or it may move through the enclosure 56 on a conveyer. This embodiment also illustrates the form of the present apparatus wherein the activated cleaning fluid mist 48 is added to and mixed with another gas flow 60. The activated cleaning fluid mist 48 mixes with the gas flow 60, and the mixed gas flow contacts the object 58. This embodiment may be implemented either as a continuous-flow system, as illustrated, or as a batch system wherein the enclosure 56 is filled with the activated cleaning fluid mist 48 or with the mixture of the activated cleaning fluid mist 48 and the gas 60 in a batch-wise fashion.

In the embodiment of FIG. 7, the enclosure 56 is formed by the walls, floor, and ceiling of a room or other structure such as a vehicle. The activated cleaning fluid mist is produced by an integrated apparatus of the type illustrated in FIG. 4, in which the mist generator 42 and the activator **46*a* are packaged together as a single unit. An optional second activator 46*b* is provided and used in the manner described in relation to FIG. 4, whose disclosure is incorporated here. The second activator 46*b* maintains the activated cleaning fluid mist in the activated state for extended periods of time, so as to allow complete decontamination of the room. The second activator 46*b* may be built into the walls, floor, or ceiling of the enclosure 56, or they may be provided as portable units that are positioned within the enclosure 56 only during the decontamination processing. The decontamination apparatus 38 of FIG. 7 decontaminates the interior walls of the room, vehicle, or other structure, as well as objects and people therein. (When people are present in an area being decontaminated using the present approach as shown in FIG. 7 and other embodiments, they may wish to wear a mask or other filter to avoid inhaling the mist, although in the case of a hydrogen peroxide mist some inhalation of the mist is not injurious.) An apparatus 38 of the type shown in FIG. 7 may be used to decontaminate a room (or rooms) in a stationary home, office, or other facility, or the interior of a movable vehicle such as an aircraft, automobile, ship, or military vehicle. The enclosure 56** may also be a protective suit worn by decontamination personnel, to provide continuing decontamination of its interior for normal operation or in the event of a leak in the protective suit.

One of the great concerns with many biowarfare microorganisms is that they are air-borne, and are transmitted from one area to another by flows of air. In a building or vehicle, once the microorganisms have entered the HVAC (heating, ventilating, and air conditioning) system in one room, they may be conveyed quickly to another part of the building. The microorganisms contaminate the entire building and the HVAC ducting, so that major cleanup efforts are required. A virtue of the present approach is that the decontamination mist is also air-borne, and readily mixes with the air-borne microorganisms to attack them. FIG. 8 illustrates an embodiment wherein the mist generator 42 and the activator 46 are built into, or temporarily inserted into, an enclosure 56 in the form of a duct of the HVAC system. The duct 62 may be part of the main duct of the HVAC system, or it may be an auxiliary duct added to the HVAC system for receiving the decontamination apparatus 38. A filter 64 is provided downstream of the mist generator 42 and activator 46 for removing particulate and any remaining mist. The filter 64 may be, for example, a porous carbon, low-restriction coalescing filter of the known type.

As illustrated by the embodiment of FIG. 8, the decontamination apparatus 38 may be used to decontaminate air and other gas flows, in addition to solid objects. FIG. 9 illustrates an embodiment wherein the decontamination apparatus 38 is used in the manner of a gas mask to furnish decontaminated breathing air for a person. The enclosure 56 is structured as a cannister having an air intake and an outlet providing air to a face mask 66 placed over the face of a person. The cleaning fluid mist is injected into the incoming air by the mist generator 42. The activator 46 may be positioned to activate the cleaning fluid mist in the manner of FIG. 2. Instead, in this case the activator 46 is positioned downstream of the air intake so that the cleaning fluid mist is first thoroughly mixed with the incoming air and thereafter activated by the activator 46. The filter 64 is provided as discussed earlier to remove particulate and any liquid remnants of the mist.

All of these embodiments in FIGS. 2–9 operate in an ambient pressure of about one atmosphere or slightly above one atmosphere, all of which are within the scope of "substantially one atmosphere ambient pressure". As noted earlier, this capability is important because most decontamination situations require the ability to achieve the decontamination without setting up vacuum chambers or pressure chambers. The mist generator produces a small overpressure of the mist as it enters the one-atmosphere environment, but does not require either a vacuum or a pressure chamber. The present approach is operable in other environments, such as less than or more than one atmosphere pressure, but does not require such higher or lower pressures to be functional.

The present invention has been reduced to practice. A number of tests of the operability of the present approach were performed, and the results of three of the test series are reported here.

In a first test series, identical cultures of serratia marcenscens were prepared by plating onto filter papers. One specimen was incubated for 24 hours at 30° C. in air as a control. Significant growth of the bacteria culture was observed. A second specimen was exposed to a 3 percent by volume aqueous hydrogen peroxide mist (which had not been activated) for 60 seconds in air at one atmosphere pressure, and thereafter incubated for 24 hours at 30° C. in air. Significant growth of the bacteria culture was observed. A third specimen was exposed to a 3 percent by volume aqueous hydrogen peroxide mist, which had been activated by passage through a 10.5 kilovolt AC arc, for 60 seconds in air at one atmosphere pressure, and thereafter incubated for 24 hours at 30° C. in air at one atmosphere pressure. This specimen showed no growth of the bacteria culture, which was killed by the treatment. After this demonstration that the activation treatment rendered the 3 percent hydrogen peroxide mist capable of preventing growth, additional respective specimens were tested using 1.5 percent, 0.75 percent, 0.3 percent, and 0 percent ("activated" water vapor only) concentration hydrogen peroxide mists for 60 seconds exposure in air at one atmosphere pressure, and incubated as described. The specimens contacted by the 1.5 percent and 0.75 percent hydrogen peroxide mists showed no growth. The specimen contacted by the 0.3 percent hydrogen peroxide mist showed very slight growth. The specimen contacted by the 0 percent hydrogen peroxide mist showed significant growth of the bacteria culture.

For a second and third test series, a duct-simulation structure was built. The duct-simulation structure was a pipe about 10 inches in diameter and 10 feet long, oriented vertically. The mist generator and activator were positioned at the top of the pipe, and a fan operating at about 350–400 cubic feet per minute gas flow was positioned at the bottom of the pipe to induce a gas flow downwardly through the pipe. Test ports were located at 1 foot, 2 feet, 4 feet, and 6 feet from the top of the pipe, and specimens to be tested were inserted at the various ports.

In the second test series, bacterial spore strips (each about ¾ inch long and ¼ inch wide) impregnated with about $10^6$ spores per strip of *bacillus stearothermophilus* were placed in each of the test ports of the duct-simulation structure. After testing, the specimens were incubated at 50° C. for seven days. In the first test specimen series, air only (no hydrogen peroxide) was flowed over the specimens for 15 seconds. Significant growth of the bacteria culture at all test ports was observed after incubation. In the second specimen series, a 6 percent by volume hydrogen peroxide mist was generated, but not activated, and flowed over the specimens for 15 seconds. The same significant growth of the bacteria culture at all test ports was observed as for the first test specimen series. In the third specimen series, this procedure was repeated, but the 6 percent hydrogen peroxide mist was activated by a 15 kilovolt AC arc. No growth of the bacteria culture was observed at any of the test ports. These results for *bacillus stearothermophilus* are significant, because this bacteria is known to be resistant to growth control using conventional, non-activated hydrogen peroxide treatments.

In the third test series, bacterial spore strips like those described above were used, except that the bacteria was *bacillus subtilis* var. *niger*. *Bacillus subtilis* var. *niger* is a recognized proxy for *bacillus anthracis*, which is in the same genus and which causes anthrax. Because of its similarity to *bacillus anthracis*, *bacillus subtilis* var. *niger* is used in laboratory testing to study growth of anthrax and its control, without the risk of contracting or spreading anthrax. In the first test specimen series, air only (no hydrogen peroxide) was flowed over the specimens for 15 seconds. Significant growth of the bacteria culture was observed after incubation of specimens from all ports. In the second specimen series, a 6 percent by volume hydrogen peroxide mist was generated, but not activated, and flowed over the specimens for 15 seconds. The same significant growth of the bacteria culture was observed at all ports as for the first test specimen series. In the third specimen series, this procedure was repeated, but the 6 percent hydrogen peroxide mist was activated by passage through a 15 kilovolt AC arc. No growth of the bacteria culture was observed at any of the ports. The present testing established that the approach of the invention controls the growth of the anthrax proxy in the duct simulation structure.

An additional feature of the present approach is that the activated cleaning fluid may be used to remove particulate matter from articles. Particulate matter may be used as the carrier for microbiological organisms. The present approach aids in removing particulate matter and any associated microbiological organisms from surfaces. Especially in embodiments such as those of FIGS. 3, 4, 6, 8, and 9, particulate matter may be removed from the contaminated region or contaminated gas flow and collected on filters, thereby removing the carrier medium of the microbiological organisms as well as destroying the exposed microbiological organisms themselves.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. A decontamination apparatus comprising:
    a source of a cleaning fluid;
    a mist generator having an input flow of the cleaning fluid and an output flow of a mist of the cleaning fluid at substantially one atmosphere ambient pressure; and
    an activator positioned to activate the mist of the cleaning fluid to produce an activated cleaning fluid mist including activatable species excited to an ion, plasma or free radical state, wherein the activator produces activating energy selected from the group consisting of electric energy and photonic energy.

2. The apparatus of claim 1, wherein the source of the cleaning fluid comprises a source of hydrogen peroxide.

3. The apparatus of claim 1, wherein the source of the cleaning fluid comprises a source of an activatable species from the group consisting of hydrogen peroxide, peracetic acid, sodium percarbonate, and gluteraldehyde.

4. The apparatus of claim 1, wherein the source of the cleaning fluid further comprises a source of a promoting species selected from the group consisting of ethylenediaminetetraacetate, isopropyl alcohol, citric acid, lactic acid, and oxalic acid, and mixtures thereof.

5. The apparatus of claim 1, wherein the source of the cleaning fluid further comprises a source of a promoting species selected from the group consisting of an alcohol, and enzyme, a fatty acid, an acid, and a chelating agent, and mixtures thereof.

6. The apparatus of claim 1, wherein the mist generator comprises of nebulizer.

7. The apparatus of claim 1, wherein the mist generator comprises a spray nozzle.

8. The apparatus of claim 1, wherein the activator produces activating energy selected from the group consisting of an AC electric field, an AC arc, a DC electric field, a pulsed DC electric field, a DC arc, an electron beam, an ion beam, a microwave beam, a radio frequency beam, and an ultraviolet beam.

9. The apparatus of claim 1, wherein the activator includes a tuner that tunes the activating energy.

10. The apparatus of claim 1, wherein the mist generator and the activator are disposed proximally, so that the activator activates the mist of the cleaning fluid as it leaves the mist generator.

11. The apparatus of claim 1, wherein the activator is located remotely from the mist generator.

12. The apparatus of claim 1, wherein the apparatus further includes an enclosure into which the mist of the cleaning fluid is directed by the mist generator.

13. The apparatus of claim 1, wherein the apparatus has no enclosure into which the mist is directed by the mist generator.

14. A method for performing decontamination, comprising the steps of producing an activated cleaning fluid mist including activatable species excited to an ion, plasma or free radical state using activating energy selected from the group consisting of electric energy and photonic energy, wherein at least a portion of the activated cleaning fluid mist is in an activated state of substantially one atmosphere ambient pressure; and contacting the activated cleaning fluid mist to a location to be decontaminated.

15. The method of claim 14, wherein the decontamination apparatus further includes an enclosure, and wherein the step of contacting occurs within the enclosure.

16. The method of claim 14, wherein the step of contacting occurs within an enclosed space.

17. The method of claim 14, wherein the step of contacting occurs in an unenclosed space.

18. The method of claim 14, wherein the step of producing includes the step of:

providing a decontamination apparatus comprising;
a source of a cleaning fluid,
a mist generator having an input flow of the cleaning fluid and an output flow of a mist of the cleaning fluid at substantially one atmosphere ambient pressure, and
an activator positioned to activate the mist of the cleaning fluid to produce the activated cleaning fluid mist.

* * * * *